United States Patent
Nicholls (10) Patent No.: US 8,377,088 B2
(45) Date of Patent: Feb. 19, 2013

(54) LANCET

(75) Inventor: Clive Nicholls, Stokenchurch (GB)

(73) Assignee: Owen Mumford Ltd., Woodstock (GB)

( * ) Notice: Subject to any disclaimer, the term of this patent is extended or adjusted under 35 U.S.C. 154(b) by 905 days.

(21) Appl. No.: 11/921,318

(22) PCT Filed: Apr. 4, 2006

(86) PCT No.: PCT/EP2006/061307
§ 371 (c)(1),
(2), (4) Date: Apr. 1, 2008

(87) PCT Pub. No.: WO2006/128752
PCT Pub. Date: Dec. 7, 2006

(65) Prior Publication Data
US 2009/0299396 A1 Dec. 3, 2009

(30) Foreign Application Priority Data
May 31, 2005 (GB) .................................. 0510895.6

(51) Int. Cl.
*A61B 17/32* (2006.01)
(52) U.S. Cl. ....................................................... 606/181
(58) Field of Classification Search .................. 606/181, 606/182, 183; 600/566, 567, 583; 604/136, 604/137, 138, 139
See application file for complete search history.

(56) References Cited

U.S. PATENT DOCUMENTS

| 4,508,534 | A | * | 4/1985 | Garver et al. ................. 604/111 |
| 5,100,428 | A | | 3/1992 | Mumford |
| 5,385,571 | A | * | 1/1995 | Morita ........................... 606/181 |
| 5,913,868 | A | | 6/1999 | Marshall |
| 6,319,209 | B1 | | 11/2001 | Kriz |
| 2003/0004520 | A1 | * | 1/2003 | Haarala et al. ................. 606/108 |
| 2004/0068282 | A1 | | 4/2004 | Bicknell |
| 2005/0015020 | A1 | | 1/2005 | LeVaughn et al. |
| 2005/0149090 | A1 | | 7/2005 | Morita et al. |

FOREIGN PATENT DOCUMENTS

| EP | 0 589 186 A1 | 3/1994 |
| EP | 0 747 006 A1 | 12/1996 |
| EP | 0790035 | 8/1997 |
| JP | 6-23505 | 3/1994 |

(Continued)

OTHER PUBLICATIONS

Translation of Japanese Office Action, dated Oct. 4, 2011, Application No. 2008-514043.

*Primary Examiner* — Ryan Severson
*Assistant Examiner* — Jonathan W Miles
(74) *Attorney, Agent, or Firm* — Young & Thompson (57) ABSTRACT

A lancet including a needle; a body for holding the needle; and a cap for shielding at least the tip of the needle; the body and/or the cap being moulded, wherein the body and the cap are bonded together during moulding, and wherein, at the interface between the body and the cap, the bonding force per area unit is less than within both the body and the cap. Also a lancet including: a needle; a body for holding the needle; and a cap for shielding at least the tip of the needle, wherein the body has a first engagement formation and the cap has a second engagement formation, wherein the engagement formations are formed such that, once the cap has been removed from the remainder of the lancet, the engagement formations can be made to engage with each other so that the cap is carried by the body.

16 Claims, 5 Drawing Sheets

FOREIGN PATENT DOCUMENTS

| | | |
|---|---|---|
| JP | 2003-153885 | 5/2003 |
| JP | 2005-111135 A | 4/2005 |
| WO | WO 96/02189 | 2/1996 |
| WO | 9927855 A1 | 6/1999 |

* cited by examiner

LANCET

The present invention relates to lancets, e.g. for pricking skin to draw a droplet of blood.

Lancets are well known in the art. Many lancets comprise a needle having a sharp tip at one end and being embedded in a body at the opposite end. For the purpose of this specification the end of the needle at which the tip is positioned will be referred to as "distal" end, and the opposite end as "proximal" end. The same terms will be used to designate the orientation or direction of other parts or movements described herein.

The needle is usually made of metal. Many known lancets also comprise a cap disposed on the distal end of the needle so as to maintain the sterility of the tip, as well as to protect the tip and the user. WO 03/071940 discloses a lancet which can be incorporated into a lancing device. This document states that the cap can be injection-moulded on to the lancet so that the cap continues into the holder (body) as a single piece. Before the lancet described in the above reference can be used it is necessary to remove the cap. This can be done by twisting or turning of the cap with respect to the body. In order to facilitate the removal of the cap the above technique proposes a weakened area at the transition from the cap to the body. The above technique suggests the use of two webs of material spaced on either side of the needle. When the cap is twisted the webs of material break and the cap can be moved in distal direction so as to remove it from the lancet.

The present inventors have perceived drawbacks with the above technique. They have appreciated that in some applications it may be desired to slide the cap off rather than to twist the cap off. Firstly, a twisting action requires two operations (first twisting the cap, then sliding it off the needle), whereas simply sliding the cap off (without the need for a twisting action) requires only one action. Secondly, especially if a non-cylindrical needle is used there is the risk that the needle becomes deformed (cork-screwed) as a result of the twisting motion, especially if the needle is made from plastics material.

Sliding the above cap off would normally require a greater force than is required when the cap is twisted off. One could reduce the required force by making the transition between the body and the cap extremely thin, but then this transition might no longer guarantee the sterility of the needle.

The present invention aims to address at least one of these concerns.

One or more aspect(s) of the invention are set out in the independent claim(s).

An embodiment disclosed herein provides a lancet comprising
 a needle;
 a body for holding the needle; and
 a cap for shielding at least the tip of the needle;
 at least one of the body and the cap being moulded,
 wherein the body and the cap are bonded together during moulding of the body or the cap, and wherein, at the interface between the body and the cap, the bonding force per area unit is less than within both the body and the cap.

In embodiments of the invention the bonding force per area unit within the body or the cap preferably means the tensile strength (per area unit) respectively within the body or the cap.

While in the above prior art a weakening is achieved by making the transition between body and cap relatively thin, in the present embodiment this is not necessarily required. It is the provision of a relatively weak bonding between the body and the cap which facilitates removal of the cap. Such a weak bonding may, for example, be achieved by first moulding the body around the proximal portion of the needle and then moulding the cap thereto over the distal portion of the needle, the body and the cap being made from different materials. Whilst a certain degree of bonding at the interface between the body and the cap is desired so as to prevent accidental separation of the cap from the body, it is desirably relatively weak so that the cap can easily be slid off the remainder of the lancet. Assuming that suitable materials are chosen for the body and the cap, the bonding between molecules of the cap and molecules of the body at the interface will be weaker than the bonding between adjacent molecules of the body or adjacent molecules of the cap.

Making the interface relatively large (but with a relatively weak bonding force) also has the advantage that a certain degree of protection against lateral loads is provided, that is loads applied radially to the cap. If a lateral load is applied to the cap of the above prior art technique there is the risk that the needle bends, the thin webs of material normally not providing any significant protection against lateral loads. Conversely, if a lateral load applied to a lancet cap according to the present invention is sufficiently large to bend the needle it will be expected also to separate the cap from the body (so the fact that the lancet is damaged can readily be detected). This is not necessarily the case with the prior art lancet, where the thin webs of material may not necessarily be severed by a load that bends the needle.

According to another embodiment disclosed therein there is provided a lancet comprising:
 a needle;
 a body for holding the needle; and
 a cap for shielding at least the tip of the needle, wherein the body has a first engagement formation and the cap has a second engagement formation, wherein the engagement formations are formed such that, once the cap has been removed from the remainder of the lancet, the engagement formations can be made to engage with each other so that the cap is carried by the body.

Whilst it is not necessarily intended that, in use, the cap of a lancet is carried by the body of that same lancet, the provision of cooperating engagement formations enables the cap of a first lancet to engage with, and to be carried by, the body of a second (similarly shaped) lancet. This may be useful if a plurality of lancets is provided as a stack.

Accordingly, another embodiment disclosed herein provides a plurality of lancets, each lancet comprising:
 a needle;
 a body for holding the needle; and
 a cap for shielding at least the tip of the needle, wherein the cap of a first lancet has an engagement formation and the body of a second lancet has a cooperating engagement formation, wherein the engagement formations are formed such that they can be made to engage with each other so that the cap of the first lancet is carried by the body of the second lancet.

Some preferred embodiments of the invention will now be described by way of example only and with reference to the accompanying drawings, in which.

Figure 1:
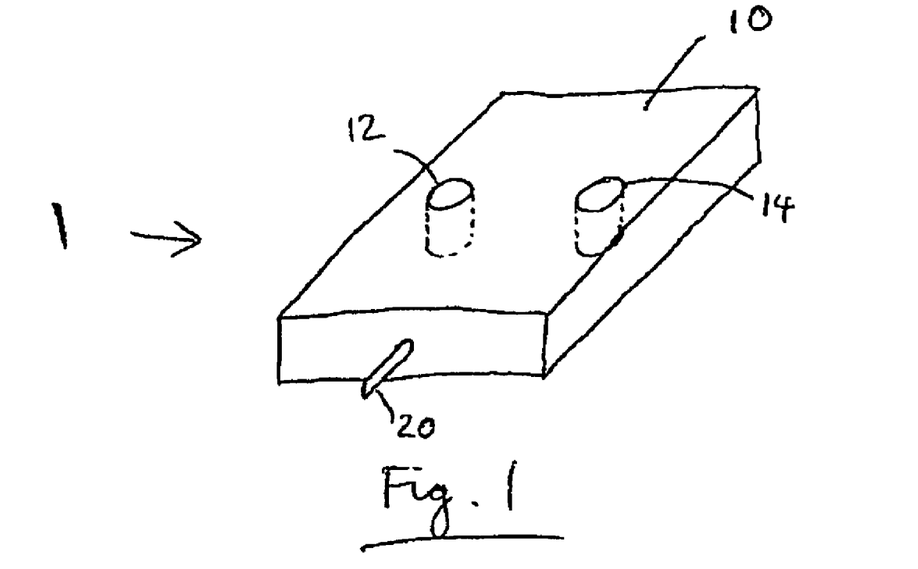
FIG. 1 shows a lancet according to a first embodiment of the invention, without cap.

As shown in FIG. 1, the lancet 1 according to the first embodiment comprises a body 10 and a needle 20 partially inserted into, and partially projecting from, the distal end of body 10. Needle 20 may e.g. be made from metal, ceramic material or plastics material. Body 10 can e.g. be made from plastics material moulded around a proximal portion of needle 20. Body 10 is formed with a number of engagement features such as holes 12 and 14 extending into, or through, body 10, e.g. in a direction generally perpendicular to the axis of the needle 20. Engagement features 12 and 14 can be used to hold and/or move body 10 in a lancing device (not shown).

Figure 2:
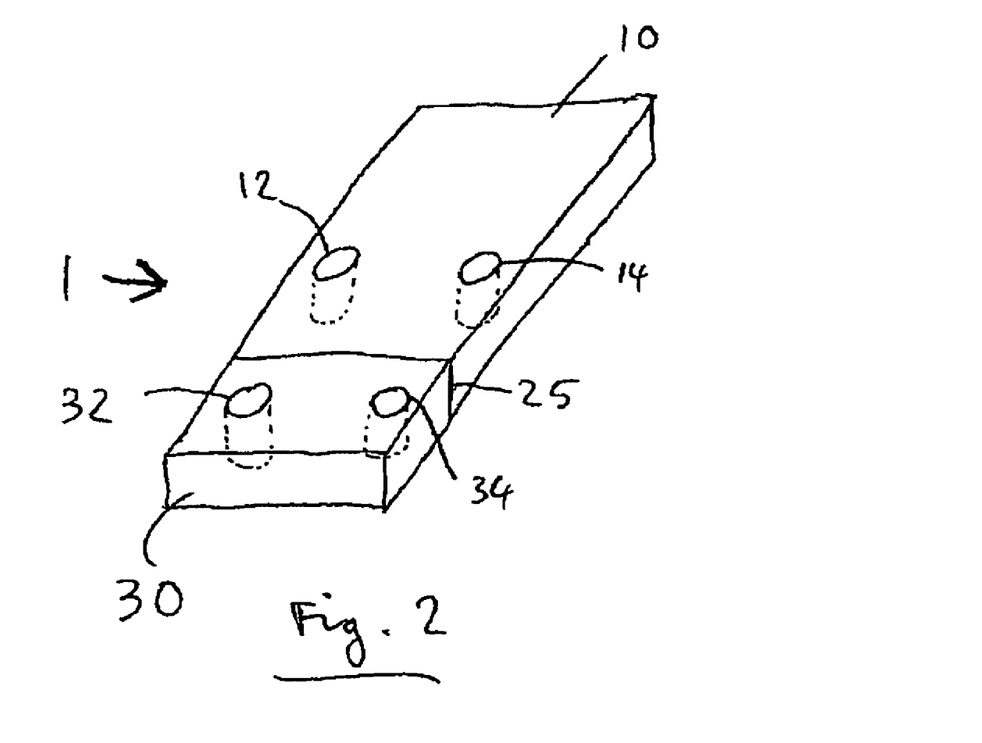
FIG. 2 shows the lancet of the first embodiment, with cap.

FIG. 2 shows the lancet of FIG. 1, before use. As compared with FIG. 1, the lancet shown in FIG. 2 additionally has a cap 30 shielding the distal portion of needle 20. Cap 30 may be made e.g. from plastics material and may be injection moulded around the distal end of needle 20.

As shown in FIG. 2, cap 30 has the same height and width as body 10. Cap 30 contacts body 10 at interface 25. This interface is relatively large as compared with the section of needle 20. This can help to maintain needle 20 sterile. It is also possible to make the cross sections of cap 30 and body 10 of different size, or of varying size, depending on manufacturing considerations or considerations as regards the use of lancet 1. However, it is preferred that cap 30 contacts body 10 over a relatively large area.

It is preferred that the body 10 is moulded around needle 20 before cap 30 is formed. It is also preferred that body 10 and cap 30 are made from different materials. For example, body 10 may first be injection moulded around needle 20 from low density polyethylene, high density polyethylene, polypropylene or polystyrene. Subsequently, cap 30 is moulded thereto, preferably from TPE, PVC, low density polyethylene, EVA, silicon rubber, polyurethane or TPU. During the moulding of the cap the cap will bond to the body, but this bond at the interface between cap 30 and body 10 will be relatively weak. Alternatively it would be possible first to mould cap 30 around the distal end of needle 20 and then to mould body 10 thereto, around the proximal portion of needle 20.

For compactness the proximal portion of needle 20 that is gripped by body 10 is between 4 and 25 mm, preferably between 5 and 15 mm, more preferably between 5 and 12 mm and yet more preferably between 6 and 8 mm. On the other hand, the distal portion of needle 20 which is gripped by cap 30 is between 2 and 5 mm, preferably about 3 mm long. It is advisable to choose the relative dimensions of proximal portion of needle 20 and distal portion of needle 20 such that needle 20 remains firmly gripped by body 10 as cap 30 is slid off.

Cap 30 may also include silicon, PTFE or oily wax. This may further reduce the grip of needle 20 within cap 30, and may also further weaken the bonding between body 10 and cap 30.

Additionally, in some embodiments it is desired that cap 30 is relatively soft, that is, the material of cap 30 should be such that it presents relatively little resistance against penetration by needle 20 if it is desired to re-cap the lancet after use. Even if needle 20 does not find its way into the bore in which it was located in cap 30 before use, re-capping should be possible without the risk of bending or breaking of needle 20.

As shown in FIG. 2, cap 30 is also provided with engagement features such as holes 32 and 34, which may be similar to holes 12 and 14 in body 10. Other types of engagement features are possible, provided that they can be used to hold and/or move cap and body with respect to each other.

In use, body 10 may be engaged at engagement features 12 and 14 by inserting two bars of a lancing device into these engagement features, and cap 30 may be engaged at engagement features 32 and 34 by inserting two different bars of the lancing device therein. Cap 30 can then be slid off in distal direction relative to body 10 by causing those bars of the lancing device which have engaged cap 30 to move in distal direction and/or by causing those bars of the lancing device which have engaged the body 10 to move in proximal direction.

A second embodiment will now be described with reference to FIGS. 3 to 9. As shown in FIG. 3, the lancet 1 again comprises a body 10 and a cap 30. The lancet also comprises a needle 20 embedded in body 10, but this is not shown in FIG. 3 (but is shown in FIG. 7). The interface 25 (indicated in FIG. 4) is much smaller than in the FIG. 2 embodiment. As with the first embodiment, cap 30 can be separated from the remainder of the lancet 1 by a relative sliding movement. Engagement features similar to those shown in FIG. 2 may be provided if desired.

Figure 3:
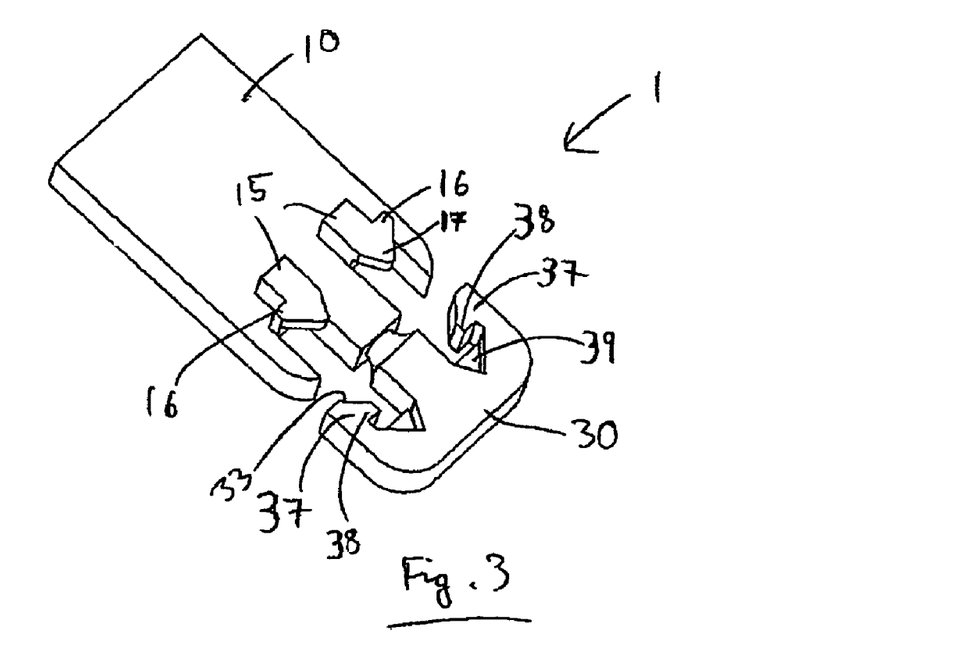
FIG. 3 shows a lancet according to a second embodiment of the invention, partly from above.

The FIG. 3 embodiment is formed with a number of engagement formations 15 on body 10 and 37 on cap 30. Engagement formations 15 stand proud from the top surface of body 10 and are generally hook shaped, with a tongue 16 projecting laterally outwardly. Engagement formations 15 may have a tapered lead-in portion 17 towards the distal end.

Similarly, engagement formations 37 on cap 30 are also generally hook-shaped, with a tongue 38 projecting inwardly. Again, the proximal end of engagement formations 37 may have a tapered lead-in portion 33.

Once cap 30 has been removed from the remainder of lancet 1 the cap 30 can be slid along the top surface of body 10 until lead-in portions 17 are adjacent lead-in portions 33. Further sliding movement of cap 30 in proximal direction will cause flexible engagement formations 37 to flex outwardly until tongues 38 have moved past tongues 16. The flexible engagement formations 37 then relax inwardly so that the engagement formations 15 are engaged with engagement formations 37. As engagement formations 15 and 37 are hook-shaped any separation of cap 30 from body 10 by means of a sliding movement in distal direction is impeded.

In order also to prevent separation of cap 30 from body 10 by means of moving cap 30 upwardly engagement formations 15 are undercut at their lead-in portions 17, and a corresponding web of material 39 is provided next to engagement formations 37. Once engagement formations 37 have been engaged with engagement formations 15 the web of material 39 will be located "under" the undercut portion 17 so that cap 30 is also restrained against movement in an upward direction. Cap 30 is thus securely held by body 10.

Figure 4:
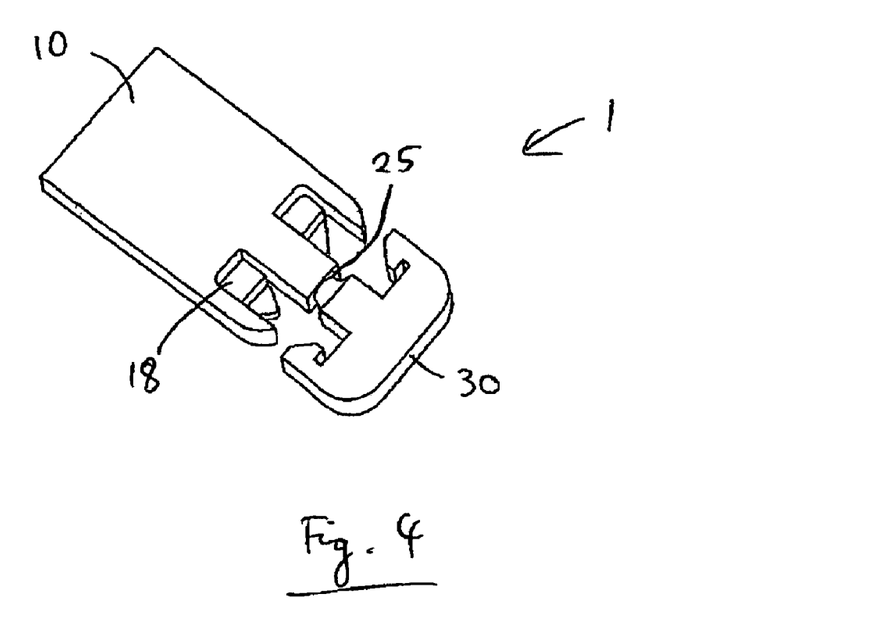
FIG. 4 shows the lancet of the second embodiment, partly from below.
Figure 5:
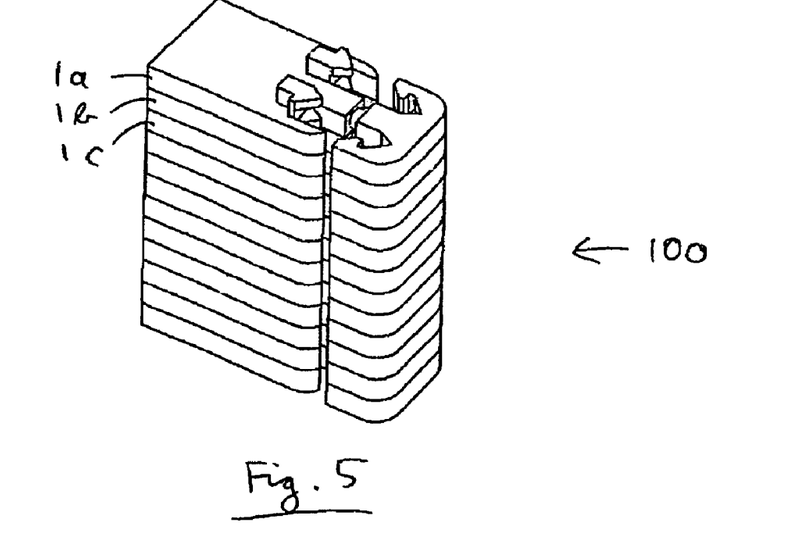
FIG. 5 shows a stack of lancets of the second embodiment, before use.

FIG. 4 shows the underside of the lancet shown in FIG. 3. A recess 18 is formed in the underside at the position where engagement formations 15 are provided on the upper side. This enables several lancets 1*a*, 1*b*, 1*c* to be provided as a stack 100, as shown in FIG. 5. Preferably, the lancets 1*a*, 1*b*, 1*c* are immediately adjacent to each other.

Figure 7:
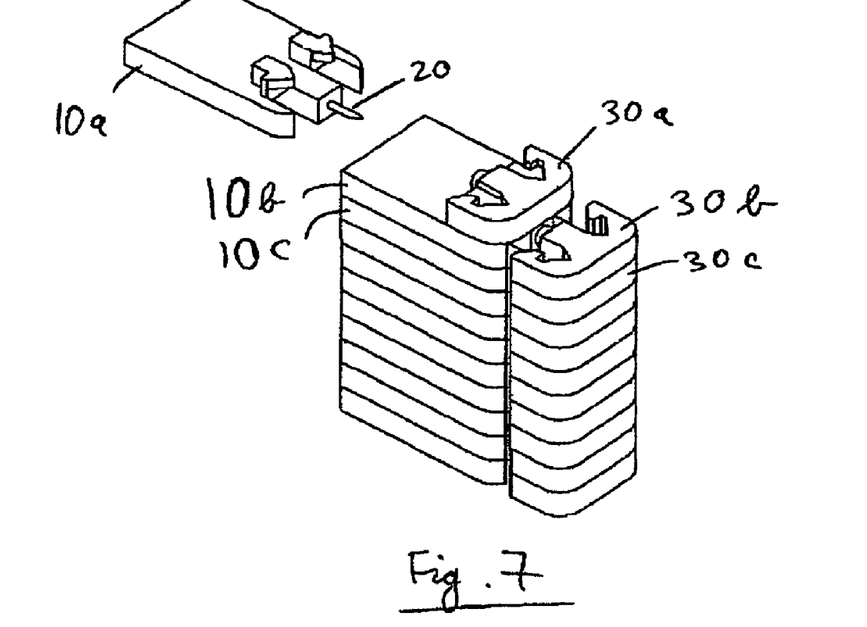
FIG. 7 shows the stack of FIG. 6, with a first lancet fully removed from the remainder of the stack.
Figure 8:
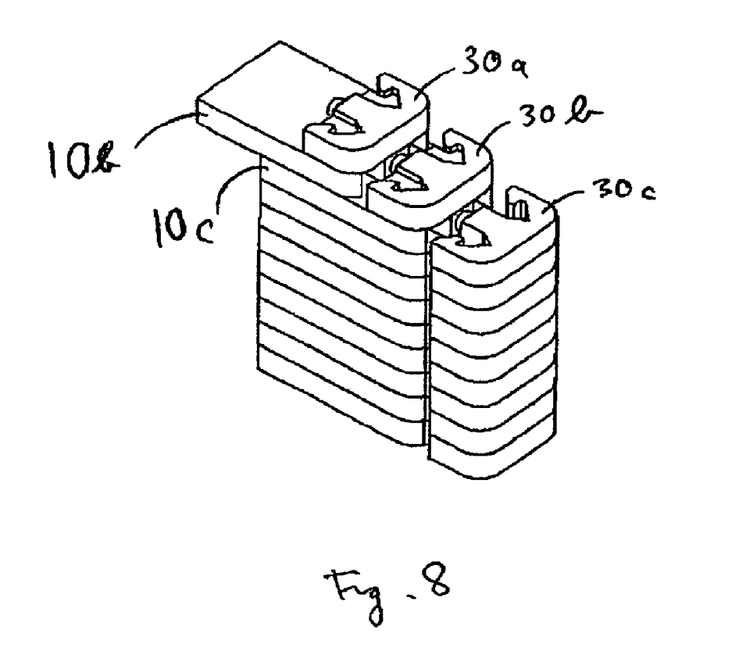
FIG. 8 shows the stack of FIG. 7, with a second lancet retracted.
Figure 9:
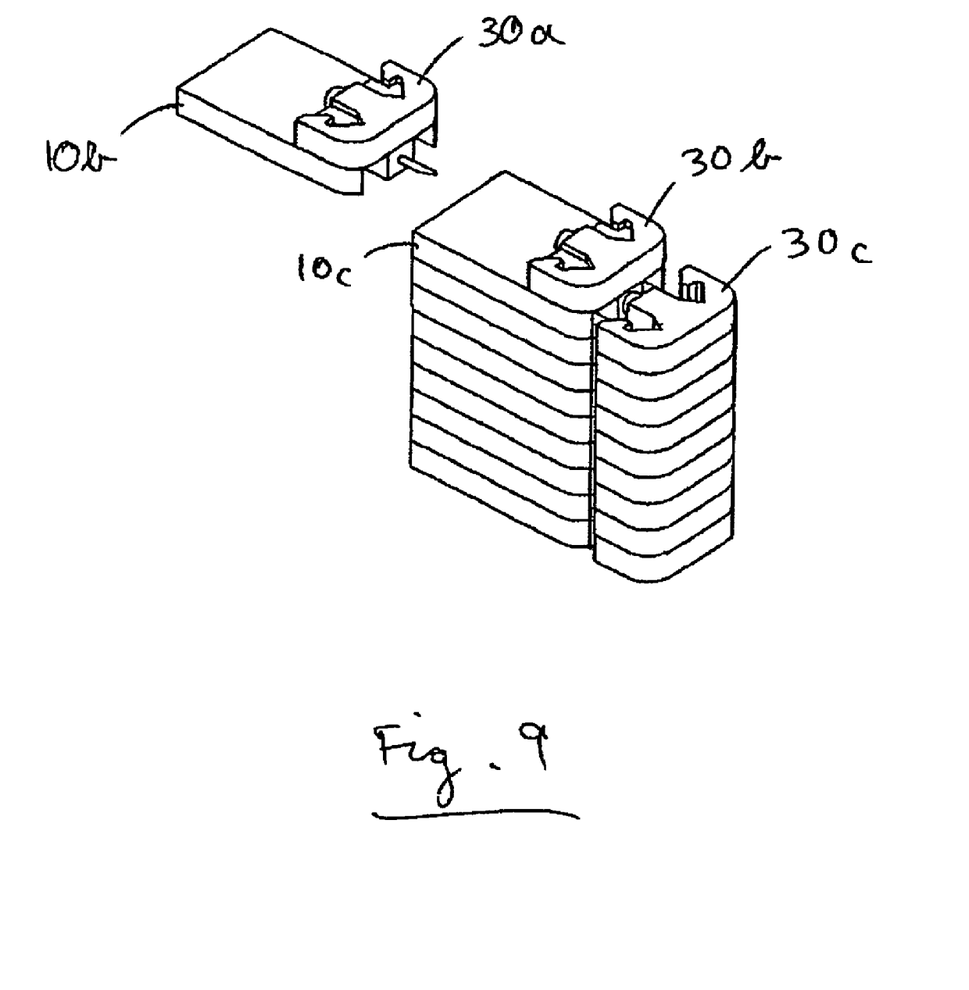
FIG. 9 shows the stack of FIG. 8, with the second lancet fully removed from the remainder of the stack.

Whilst it has been described above that cap 30 of a lancet can be caused to engage with body 10, the preferred use of the lancets is not such that a cap 30 of a particular lancet is caused to engage with the body 10 of that same lancet. However, the cap 30*a* of a first lancet 1*a* can be brought into engagement with the body 10*b* of a second lancet 1*b*. To this end a stack as shown in FIG. 5 is provided. The topmost lancet 1a is then retracted in proximal direction as indicated by the arrow in FIG. 6. This causes the engagement formations 37 of cap 30a to engage with engagement formations 15 of body 10b. The bonding force between body 10a and cap 30a of lancet 1a needs to be stronger than the force that is required to bring engagement formations 37 into engagement with engagement formations 15. Once cap 30a is engaged with body 10b the cap 30a is separated from body 10a if body 10a is moved further in proximal direction. This state is shown in FIG. 7, where the uncapped lancet 1a (i.e. body 10a and needle 20) can be used to prick skin. Cap 30a remains on body 10b. As shown in FIG. 8, the next lancet 1b can then be retracted in proximal direction. This moves body 10b (which carries cap 30a) and cap 30b into the position shown in FIG. 8. Cap 30b is then engaged with body 10c of lancet 1c, and further retraction of body 10b fully separates body 10b from cap 30b. The uncapped lancet 1b (i.e. body 10b and needle 20) can then be used to prick skin, still carrying cap 30a. This is shown in FIG. 9. In this manner lancets ready for use can be separated from stack 100 simply by retracting the body of the topmost lancet in the stack.

As there is no lancet "under" the last lancet in the stack a set of "dummy" engagement formations may be provided, e.g. formed on the bottom of a housing in which stack 100 may be provided. The last lancet may then be retracted, causing the last cap to engage with the dummy engagement formations of the housing.

An additional advantage of the second embodiment is that there are no loose caps which could e.g. interfere with the operation of the lancing device which may be used to lance the stack of lancets.

Figure 6:
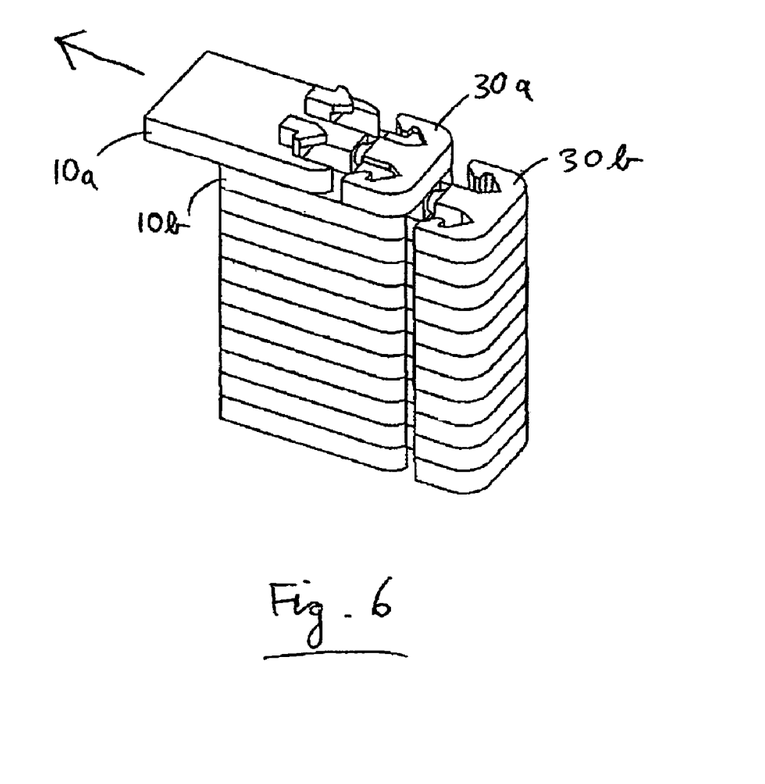
FIG. 6 shows the stack of lancets shown in FIG. 5, with one lancet retracted.

In connection with FIG. 6 it has been stated above that the bonding force between body 10a and cap 30a of lancet 1a needs to be stronger than the force that is required to bring engagement formations 37 into engagement with engagement formations 15. In an alternative, third embodiment this is not necessarily the case. The lancets may be formed according to the second embodiment. However, in the third embodiment the lancets are initially not pulled in proximal direction by their body 10 but are pushed in proximal direction by the application of a force onto their cap 30 until the cap 30 has engaged with the body 10 of the lancet below. Subsequently the body 10 of the lancet that has been pushed in proximal direction is pulled in the same manner as described in connection with the second embodiment, so that cap 30 becomes separated from the body. In this way the bonding force between the cap and the body may be made particularly weak.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A lancet comprising:
   a needle;
   a body for holding the needle so that the needle partially projects from a surface of the body; and
   a cap for shielding at least the tip of the needle;
   at least one of the body and the cap being molded,
   wherein the body and the cap are bonded together at an interface between the body and the cap, the interface between the body and the cap being formed by the distal most surface of the body and the proximal most surface of the cap, and wherein the bonding force per area unit at the interface is less than within both the body and the cap.

2. A lancet according to claim 1, wherein the cap is in direct contact with the body.

3. A lancet according to claim 1, wherein the interface between the body and the cap is substantially free of any adhesive.

4. A lancet according to claim 1, wherein the body and the cap are bonded together over an area which corresponds to at least half of the maximum cross-sectional area of the body or the cap.

5. A lancet according to claim 1, produced by first molding one of the body and the cap and then molding the other of the body and the cap thereto.

6. A lancet according to claim 1, wherein the cap is made from a material which allows the needle to penetrate into the cap substantially without the risk of bending or breaking of the needle.

7. A lancet according to claim 1, wherein the cap includes silicon, PTFE or oily wax.

8. A lancet according to claim 1, wherein the body comprises low density polyethylene, high density polyethylene, polypropylene or polystyrene.

9. A lancet according to claim 1, wherein the cap is made from TPE, PVC, low density polyethylene, EVA, silicon rubber, polyurethane or TPU.

10. A lancet according to claim 1, wherein the needle is embedded in both the body and the cap.

11. A lancet according to claim 1, wherein the needle is embedded in both the body and the cap, and the needle is gripped in the body much more firmly than in the cap.

12. A lancet according to claim 1, wherein the needle is embedded in both the body and the cap, and the needle is gripped in the body over a length of between 4 and 25 mm.

13. A lancet according to claim 1, wherein the needle is embedded in both the body and the cap, and the needle is embedded in the cap over a length of between 2 and 5 mm.

14. A lancet according to claim 1, wherein the cap and/or the body comprises one or more engagement features facilitating the removal of the cap from the remainder of the lancet by applying a separating force between the body and the cap in a direction substantially parallel to the axis of the needle.

15. A lancet according to claim 1, wherein the force required to separate the cap from the body is between 0.5 and 8 N.

16. A method of making a lancet according to claim 1, comprising first molding one of the body and the cap around a portion of the needle, and, thereafter, molding the other of the body and the cap thereto.

* * * * *

UNITED STATES PATENT AND TRADEMARK OFFICE
CERTIFICATE OF CORRECTION

PATENT NO.       : 8,377,088 B2  
APPLICATION NO. : 11/921318  
DATED            : February 19, 2013  
INVENTOR(S)      : Clive Nicholls Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1104 days.

Signed and Sealed this

First Day of September, 2015

Michelle K. Lee
*Director of the United States Patent and Trademark Office*